(12) United States Patent
Abedi

(10) Patent No.: US 6,524,863 B1
(45) Date of Patent: Feb. 25, 2003

(54) HIGH THROUGHPUT HPLC METHOD FOR DETERMINING LOG P VALUES

(75) Inventor: Jaleh Abedi, Raleigh, NC (US)

(73) Assignee: Scynexis Chemistry & Automation, Inc., Durham, NC (US)

(*) Notice: Subject to any disclaimer, the term of this patent is extended or adjusted under 35 U.S.C. 154(b) by 177 days.

(21) Appl. No.: 09/625,905

(22) Filed: Jul. 26, 2000

Related U.S. Application Data

(60) Provisional application No. 60/147,093, filed on Aug. 4, 1999.

(51) Int. Cl.[7] ............................................. G01N 30/02
(52) U.S. Cl. ..................... 436/161; 73/61.52; 73/61.56; 210/656; 210/662
(58) Field of Search .................. 436/161; 73/61.52, 73/61.56; 210/656, 662

(56) References Cited

U.S. PATENT DOCUMENTS

| | | |
|---|---|---|
| 3,589,867 A | 6/1971 | Heinz et al. |
| 3,680,967 A | 8/1972 | Engelhardt |
| 3,853,010 A | 12/1974 | Christen et al. |
| 4,798,095 A | 1/1989 | Itoh |
| 4,835,707 A | 5/1989 | Amano et al. |
| 5,267,178 A | 11/1993 | Berner |
| 5,273,715 A | 12/1993 | Bridgham et al. |
| 5,301,261 A | 4/1994 | Poole et al. |
| 5,324,483 A | 6/1994 | Cody et al. |
| 5,434,971 A | 7/1995 | Lysakowski, Jr. |
| 5,463,564 A | 10/1995 | Agrafiotis et al. |
| 5,489,678 A | 2/1996 | Fodor et al. |
| 5,503,805 A | 4/1996 | Sugarman et al. |
| 5,525,464 A | 6/1996 | Drmanac et al. |
| 5,527,681 A | 6/1996 | Holmes |
| 5,541,061 A | 7/1996 | Fodor et al. |
| 5,545,531 A | 8/1996 | Rava et al. |
| 5,547,839 A | 8/1996 | Dower et al. |
| 5,552,270 A | 9/1996 | Khrapko et al. |
| 5,556,762 A | 9/1996 | Pinilla et al. |
| 5,574,656 A | 11/1996 | Agrafiotis et al. |

(List continued on next page.)

FOREIGN PATENT DOCUMENTS

| | | |
|---|---|---|
| DE | 196 05 814 | 8/1997 |
| EP | 08 82500 | 12/1998 |
| EP | 0 903 176 | 3/1999 |
| FR | 2 760 843 | 9/1998 |
| WO | 95 1559 | 1/1995 |
| WO | 96 05488 | 2/1996 |

OTHER PUBLICATIONS

Masereel et al, J. Pharm. Pharmacol., vol. 44 (1992), pp. 589–593.*
Valko et al, Anal. Chem., vol. 69 (1997), pp. 2022–2029.*
Chemical Abstract No. 129:196029: Valko et al., Journal of Chromaotgraphy, A (1998), 797 (1 + 2), 41–55.*

(List continued on next page.)

Primary Examiner—Jan Ludlow
(74) Attorney, Agent, or Firm—Burns Doane Swecker & Mathis LLP

(57) ABSTRACT

Methods for calculating Log P values for organic compounds are disclosed. The methods allow identification of compounds in a library with a desired Log P value. The method can be used to minimize the number of compounds in a given combinatorial or lead generation library which need to be further characterized and/or assayed. The Log P value is preferably obtained while the purity of the compounds is being determined. Preferably, the Log P value is correlated to the retention time on an HPLC column, such that the retention time equals the Log P value.

12 Claims, 3 Drawing Sheets

U.S. PATENT DOCUMENTS

| | | |
|---|---|---|
| 5,595,664 A | 1/1997 | Sanford et al. |
| 5,609,826 A | 3/1997 | Cargill et al. |
| 5,639,603 A | 6/1997 | Dower et al. |
| 5,641,634 A | 6/1997 | Mandecki |
| 5,658,799 A | 8/1997 | Choperena et al. |
| 5,670,054 A | 9/1997 | Kibbey et al. |
| 5,679,773 A | 10/1997 | Holmes |
| 5,684,711 A | 11/1997 | Agrafiotis et al. |
| 5,690,893 A | 11/1997 | Ozawa et al. |
| 5,693,292 A | 12/1997 | Choperena et al. |
| 5,708,153 A | 1/1998 | Dower et al. |
| 5,712,171 A | 1/1998 | Zambias et al. |
| 5,736,412 A | 4/1998 | Zambias et al. |
| 5,741,462 A | 4/1998 | Nova et al. |
| 5,757,659 A | 5/1998 | Arai et al. |
| 5,766,481 A | 6/1998 | Zambias et al. |
| 5,772,962 A | 6/1998 | Uchida et al. |
| 5,798,035 A | 8/1998 | Kirk et al. |
| 5,807,754 A | 9/1998 | Zambias et al. |
| 5,862,514 A | 1/1999 | Huse et al. |
| 5,874,214 A | 2/1999 | Nova et al. |
| 5,901,069 A | 5/1999 | Agrafiotis et al. |
| 5,925,562 A | 7/1999 | Nova et al. |
| 5,938,932 A | 8/1999 | Connelly et al. |
| 5,942,387 A | 8/1999 | Hollinshead |
| 5,948,360 A | 9/1999 | Rao et al. |
| 5,993,662 A | 11/1999 | Garr et al. |

OTHER PUBLICATIONS

Brenner, S., et al., "Encoded combinatiorial chemistry", *Proc, Nat'l. Acad, Sci. USA*, 89: 5381–5383, 1992.

DeWitt, S. H., et al., "Combinatorial Organic Synthesis Using Parke–Davis's Diversomer Method", *Acc. Chem. Res.*, 29(3): 114–122, 1996.

Griffey, R. H., et al., "Rapid Deconvolution of combinatorial Libraries using HPLC Fractionation", *Tetrahedron, NL, Elsevier Sci. Pub.*, 54(16): 4067–4076, 1998.

Harris, S., et al., "High Throughput Analysis & Purification: The new Paradigm", *MDS Panlabs*, 1–13, 1998.

Josses, P, et al., "Carrying out Multiple Reactions in Organic Synthesis with a Robot", *Advances in Laboratory Automation Robotics*, 5: 463–475, 1990.

Kibbey, C. E., "An Automated System for the Purification of Combinatorial libraries by Preparative LC/MS", *Laboratory Robotics and Automation*, 9: 309–321, 1997.

Lindsey, J. S., "A retrospective on the automation of laboratory synthetic chemistry", *Laboratory Automation & Information Management*, 17(1): 15–45, 1992.

Rotstein, S., et al., "GroupBuild: A Fragment–Based Method for *De Novo* Drug Design", *J. Med. Chem.*, 36: 1700–1710, 1993.

Rudge, D. A., "The automation of solution phase synthetic chemistry using XP Zymate™ laboratory robotic systems", *Laboratory Automation & Information Management*, 33(2): 81–86, 1997.

Schultz, L., et al., "High Throughput Purification of Combinatorial Libraries", *Bio & Med. Chem. Ltrs.*, 8: 2409–2414, 1998.

Testa, B., "The Concept of Molecular Structure in Structure–Activity Relationship Studies and Drug Design", *Med. Res. Rev.*, 11 (1): 38–48, 1991.

"Techniques and Experiments for Organic Chemistry", 2nd Edition, 56–60, 1977.

Weller, H. N., et al., "High throughput analysis and purification in support of automated parallel synthesis", *Molecular Diversity*, 3: 61–70, 1997.

*Chemical Analysis*, 91:234–278 (Chapter 11), Wiley and Sons, New York (1987).

Bishop, C.A., et al., "The Preparative Separation of Synthetic Peptides on Reversed–Phase Silica Packed in Radially Compressed Flexible–Walled Columns," *J. Liquid Chromatography*, 4(4):661–680 (1981).

Bishop, C.A., et al., "High Performance Liquid Chromatography of Amino Acids, Peptides and Proteins XXI. The application of preparative reversed–phase high–performance liquid chromatography for the purification of a synthetic underivatised peptide," *Journal of Chromatography*, 192:222–227 (1980).

Knighton, D.R., et al., "Facile, Semi–Preparative, High–Performance Liquid Chromatographic Separation of Synthetic Peptides Using Ammonium Bicarbonate Buffers," *Journal of Chromatography*, 249:193–198 (1982).

Mirrlees, M.S., et al., "Direct Measurement of Octanol–Water Partition Coefficients by High–Pressure Liquid Chromatography," *J. Med. Chem.*, 19(5):615–619 (1976).

Zeng, L., et al., "Automated analytical/preoperative high–performance liquid chromatography–mass spectrometry system for the rapid characterization and purification of compound libraries", *J. of Chrom. A.*, (Elseiver Science B.V.) 794: 3–13, 1998.

\* cited by examiner

Log P vs. Capacity Factor

HIGH THROUGHPUT HPLC METHOD FOR DETERMINING LOG P VALUES

This application claims benefit of Provisional Application No. 60/147,093 filed Aug. 4, 1999.

FIELD OF THE INVENTION

The present invention generally relates to the determination of log P values for libraries of compounds, for example, combinatorial and/or lead generation libraries.

BACKGROUND OF THE INVENTION

For many drugs and pesticides, there is a relationship between their physiological activity and their hydrophobicity. The classical method for determining the hydrophobicity of a compound is to determine the logarithm of the partition of the compound in water and n-octanol. When a relationship between chromatographic retention data and logarithm of n-octanol/water partition coefficients (Log P) can be established, the hydrophobicity of a compound can be determined chromatographically rather than using the shake flask method. The n-octanol/water partition system is not necessarily an ideal one. Chromatographically derived measures can be even more reliable, depending on the reliability of the particular HPLC method.

There are advantages to using a chromatographic method versus the shake flask method. For example, the chromatographic method is faster and more suitable for compounds containing impurities. No quantitative measure is required, and the method can be applied to volatile compounds.

Numerous HPLC methods for determining Log P values have been developed. One of the limitations associated with using HPLC is that special care must be taken when one is evaluating ionizable compounds. Often, the calculation of the Log P requires a correction for the dissociation factor (CD) for the compound.

One method for determining Log P using an HPLC method involves coating a silanized Kieselguhr support with water-saturated n-octanol and using an n-octanol saturated buffer as the eluent. Mirrlees et al., *J. Med. Chem.*, 19:615 (1976). Log P values in the range of between −0.3 and 3.7 can be obtained by varying the column length and flow rate. Correlations have also been made between Log P and the log of the retention volume on a C18 column. Numerous other means for correlating Log P and HPLC are known, each of which has certain advantages and disadvantages. Chemical Analysis, 91:234-278 (Chapter 11), Wiley and Sons, New York, (1987)

Retention parameters obtained from HPLC measurements (log k') can be used to obtain information regarding the hydrophobicity of compounds. The retention data obtained with a hydrophobic stationary phase and using water as the mobile phase can be used directly, although this typically results in extended retention times. Isocratic data, measured at certain eluent compositions (typically as log $k'_x$, for a given eluent composition X), can be used to calculate Log P data. Also, when using aqueous solutions which contain water miscible organic solvents such as methanol, acetonitrile, and acetone, chromatographic data can be extrapolated to the point at which there is 0% organic solvent in the mobile phase, which permits one to do the HPLC runs faster than when water alone is used and still obtain reasonably reliable results.

However, the method tends to be limited in that only a limited amount of water-miscible organic solvents can be present in the water. If too much organic solvent is present, the linear relationship between the concentration and the log $k'_w$ may no longer exist. Several authors have advocated using isocratic log $k'_x$ values rather than log $k'_w$ values.

A further limitation of classical HPLC methods for determining Log P values is that they often rely on correlation between the capacity factor and Log P, and this correlation is typically close only for related compounds, and is poorer for compounds containing different functional groups.

In spite of the limitations associated with the use of too much organic solvent and the problems associated with analyzing highly polar ionizable compounds on a reverse phase column, HPLC methods are still applicable for determining Log P values for a large number of organic compounds, based on the linear relationship between log P and log k'. Nevertheless, it would be advantageous to provide additional HPLC methods which overcome the limitations of these methods. Further, it would be advantageous to provide useful methods for determining the hydrophobicity of libraries of compounds. The present invention provides such methods.

SUMMARY OF THE INVENTION

Methods and apparatus for high through Log P determination of libraries of compounds, for example, combinatorial or lead generation libraries, are disclosed. The methods involve obtaining a number of compounds to be evaluated, and using an HPLC method to determine the Log P value for the compounds. In a preferred embodiment, the purity and Log P values for the compounds are determined simultaneously. In another preferred embodiment, the compounds are subjected to Log P determination and bioassay for determination of their bioactivity. Compounds with desired bioactivity and Log P can be subject to further examination, and evaluated separately from compounds which have the desired Log P but not the desired activity and compounds which have the desired activity but not the desired Log P.

The method is advantageous in that it allows rapid determination of compounds not only with the desired bioactivity but also with the desired hydrophobicity/hydrophilicity for the intended use. Large numbers of compounds in combinatorial libraries can be screened and the most effective compounds for a particular indication rapidly identified.

In another preferred embodiment, the method allows the Log P determination to be calculated based on retention time, rather than an isocratic method (which does not use a gradient).

DETAILED DESCRIPTION OF THE INVENTION

Figure 1:
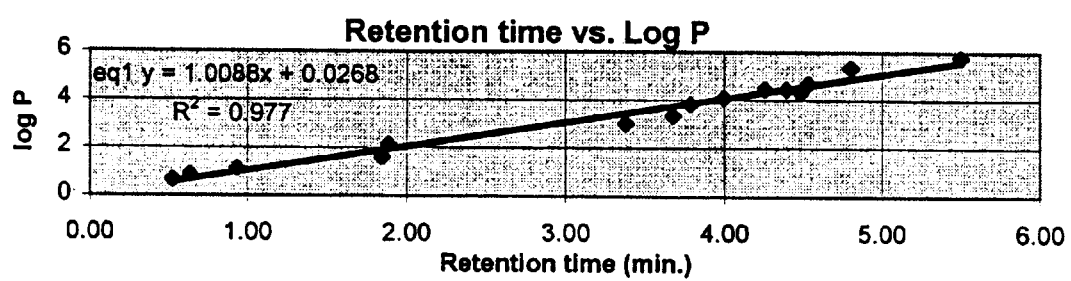
FIG. 1 is a plot of log P versus retention time (min.) for a series of standards.

Methods and apparatus for determining the Log P values and, optionally, the purity, for libraries of compounds, are disclosed. The methods can be broadly applied to combinatorial libraries and lead generation libraries, which can optionally be characterized and/or evaluated for efficacy, for example, in bioassays.

In one embodiment, the method allows one to correlate the Log P values of compounds with the retention time of the compound on an HPLC column, preferably while simultaneously determining the purity of the compounds. In this method, the solvent gradient and flow rate for a particular column and column packing can be adjusted such that the retention time for a series of standards equals the log P values as determined using a shake flask method. Then, once the system is set up such that retention time is approximately equal to Log P, the compounds can be evaluated. In this embodiment, it is preferred to use a short column (less than or equal to 5×50 mm column), preferably with a column packing (sorbent) which has a relatively small particle size (5 microns or less), because the void volume of the column can be neglected.

In a preferred embodiment, the information regarding the purity, identity, Log P and bioactivity of the compounds can be stored in a database, and compounds with the desired Log P value and bioactivity identified in a rapid manner from a library of compounds.

As used herein, an "HPLC compatible detector" is a detector suitable for use in an HPLC system which is capable of providing a detectable signal upon elution of a compound peak. For example, a detector capable of generating a signal when a compound elutes from the compound is an HPLC compatible detector. Where component absorbance varies widely, it may be necessary to utilize more than one detector. A detector capable of detecting a desired component is not an "incompatible" detector due to its inability to detect a non-desired peak.

HPLC Devices

Displacement chromatography (an example of which is HPLC) is based on the principle that in a sample the balance between stationary phase (SP) and mobile phase (MP) is shifted the direction of SP. Single components of a sample displace each other like a train and the displacing agent with the greater affinity to SP pushes this train by fractions out of the column. HPLC chromatography is one of the most well known examples of displacement chromatography.

An HPLC device typically includes at least the following components: a column, packed with a suitable stationary phase, a mobile phase, a pump for forcing the mobile phase through the column under pressure, and a detector for detecting the presence of compounds eluting off of the column. The devices can optionally include a means for providing for gradient elution, where the solvent system is varied during the purification.

Routine methods and apparatus for carrying out HPLC separations are well known in the art, and are described, for example, in the following references: *J. Chromatography*, 192:222–227 (1980), *J. Liquid Chromatography* 4:661–680 (1981), and *J. Chromatography*, 249:193–198 (1982).

Suitable stationary phases are those in which the compound of interest elutes. Preferred columns are reverse phase columns, which may be natural (silica gel with alkyl chains of different lengths) or a synthetic crosslinked polymer (consisting of styrene and divinylbenzene). The particle size of the stationary phase is within the range from a few $\mu$m to several 100 $\mu$m. The most preferred stationary phase is a $C_{18}$ column.

In some embodiments, the pH of the mobile phase must be moderately acidic because of a lower stability of various compounds, such as ammonium salts, to alkaline media, and is adjusted by the concentration of the acid or by the formation of an appropriate buffer.

Suitable detection devices include mass spectrometers, evaporated light scattering (ELSD) and ultraviolet (UV) detectors. The methods described herein can use these detectors alone or in combination.

Log P Method In one embodiment, the method involves performing the following steps:

a) selecting a library of compounds to evaluate, b) determining the Log P value for the compounds, optionally while simultaneously determining the purity of the compounds, using an HPLC method, c) optionally chemically characterizing the compounds, and d) optionally subjecting the compound to assays to determing their bioactivity.

In a preferred embodiment, the Log P values are determined from the retention time of the compounds on the HPLC column, using the preferred method described below in Example 1 or other methods which, using, for example, different solvents, injection size, flow rates, column size and/or column packing still provide a direct relationship between retention time and Log P values. Preferably, the method involves gradient elution, where the gradient is used to force compounds with a certain hydrophobicity to elute at a certain time interval.

Using such methods, the retention time may itself equal Log P or may be the retention time multiplied by the slope of the line correlating the known log P values for a set of compounds with the retention time of such compounds as determined using a given HPLC method. Using an appropriate HPLC method, such as the one described herein in Example 1, it is possible to obtain a linear relationship between the retention time and the Log P value. Other methods than that described in Example 1, but which provide a linear relationship between retention time and log P can also be used and are intended to be within the scope of the invention. Alternatively, other methods for determining Log P values using HPLC, including isocratic HPLC methods known in the art, can be used.

By determining the Log P values of the compounds, preferably while their purity is being determined, compounds which do not have the desired Log P values can be discarded, and only those with the desired Log P values (or hydrophobicity) can be characterized and evaluated for bioactivity. This permits more rapid evaluation of the library.

The following optional steps can optionally be performed. The information on the compound (i.e., the UV absorbance and MS information) can be stored in a relational database, preferably with other information about the compound (i.e., synthesis conditions, bioassay information, yield, etc.). The compound can be further characterized, for example, by $^1$H NMR. To more rapidly evaluate the purity of the compounds, the HPLC can include two or more columns, one of which is used to determine the Log P values for the compounds while the other is being cleaned and regenerated. This step removes the chromatographic equilibration downtime.

Types of Compounds which can be Evaluated Using the Methods

The Log P values and purity of virtually any organic compound which is capable of being eluted on an HPLC column can be determined using the methods described herein. Preferably, the compounds are part of a library of compounds, more preferably, a lead generation or combinatorial library of compounds.

The term "library" refers to at least 3, preferably from $10^2$ to $10^9$ and more preferably from $10^2$ to $10^4$ compounds. Preferably, these compounds are prepared as a multiplicity of compounds in a single solution or reaction mixture which permits facile synthesis thereof. Each member of the library of compounds can be isolated and, optionally, characterized.

Typically, the compounds have a core structure which can be modified at least one position, preferably two or more positions, with a variety of different functional groups, in order to generate a library, for example, a combinatorial or lead optimization library of compounds.

Typical core structures are linear, branched or cyclic organic compounds that include at least three carbon atoms and at least one, and preferably at least two sites capable of undergoing a reaction to change the structure, usually by the addition of other molecules to the reactive site.

Examples of families of insecticides include 1-aryl pyrazoles, pyrroles, pyrrolidones, and nicotinic acid derivatives. However, ligand compounds which may bind to the appropriate binding site may be, for example, steroids, hormones, peptides, proteins, oligonucleotides, oligoribonucleotides, enzymes, and the like.

Suitable core structures include, but are not limited to: peptides, proteins, oligonucleotides, oligoribonucleotides, oligosaccharides, alkaloids, quinolines, isoquinolines, benzimidazoles, benzothiazoles, purines, pyrimidines, thiazolidines, imidazopyrazinones, oxazolopyridines, pyrroles, pyrrolidines, imidazolidones, guinolones, amino acids, macrolides, penems, saccharides, xanthins, benzothiadiazine, anthracyclines, dibenzocycloheptadienes, inositols, porphyrins, corrins, and carboskeletons presenting geometric solids (e.g., dodecahedrane). The core structures can be derived from naturally occurring compounds, or can include non-natural modifications (i.e., non-naturally occurring amino acids and nucleotides).

Suitable modifications for the core structures include:

1) amino acid derivatives, which include, for example, natural and synthetic amino acid residues including all of the naturally occurring alpha amino acids, species having derivatives, variants or mimetics of the naturally occurring side chains; N-substituted glycine residues; natural and synthetic species known to functionally mimic amino acid residues, such as statin, bestatin, etc.

2) nucleotide derivatives, which includes natural and synthetic nucleotides, such as adenosine, thymine, guanidine, uridine, cytosine, derivatives of these and variants and mimetics of the purine ring, the sugar ring, the phosphate linkage and combinations of some or all of these. Nucleotide probes (between 2 and 25 nucleotides) and oligonucleotides (more than 25 nucleotides) including all of the various possible structural modifications; homo and hetero-synthetic combinations and permutations of the naturally occurring nucleotides; derivatives and variants containing synthetic purine or pyrimidine species, or mimics of these; various sugar ring mimetics; and a wide variety of alternate backbone analogs, including but not limited to phosphodiester, phosphorothionate, phosphorodithionate, phosphoramidate, alkyl phosphotriester, sulfamate, 3'-thioformacetal, methylene(methylimino), 3-N-carbamate, morpholino carbamate and peptide nucleic acid analogs.

3) a carbohydrate derivative, which would include natural physiologically active carbohydrates; related compounds, such as glucose, galactose, sialic acids, beta-D-glucosylamine and nojorimycin, which are both inhibitors of glucosidase; pseudo sugars, such as 5a-carba-2-D-galactopyranose, which is known to inhibit the growth of Klebsiella pneumonia (n=1); synthetic carbohydrate residues and derivatives of these (n=1) and all of the complex oligomeric permutations of these as found in nature, including high mannose oligosaccharides, the known antibiotic streptomycin (n>1).

4) a naturally occurring or synthetic organic structural motif. The term "motif" is defined as an organic molecule having or containing a specific structure that has biological activity, such as a molecule having a complementary structure to an enzyme active site, for example. This term includes any of the well known basic structures of pharmaceutical compounds including pharmacophores, or metabolites thereof. These basic structures include beta-lactams, such as penicillin, known to inhibit bacterial cell wall biosynthesis; dibenzazepines, known to bind to CNS receptors and used as antidepressants; polyketide macrolides, known to bind to bacterial ribosymes, etc. These structural motifs are generally known to have specific desirable binding properties to ligand acceptors.

5) a reporter element, such as a natural or synthetic dye or a residue capable of photographic amplification which possesses reactive groups that may be synthetically incorporated into the sulfaminimide structure or reaction scheme, and may be attached through the groups without adversely interfering or affecting with the reporting functionality of the group. Preferred reactive groups are amino, thio, hydroxy, carboxylic acid, carboxylic acid ester, particularly methyl ester, acid chloride, isocyanate alkyl halides, aryl halides and oxirane groups.

6) an organic moiety containing a polymerizable group such as a double bond, or other functionalities capable of undergoing condensation polymerization or copolymerization. Suitable groups include vinyl groups, oxirane groups, carboxylic acids, acid chlorides, esters, amides, azlactones, lactones and lactams. Other organic moiety such as those defined for R and R' may also be used.

7) a macromolecular component, such as a macromolecular surface or structures which may be attached to the sulfaminimide modules via the various reactive groups outlined above, in a manner where the binding of the attached species to a ligand-receptor molecule is not adversely affected and the interactive activity of the attached functionality is determined or limited by the macromolecule. Examples of macromolecular components include porous and non-porous inorganic components, such as, for example, silica, alumina, zirconia, titania and the like, as commonly used for various applications, such as normal and reverse phase chromatographic separations, water purification, pigments for paints, etc.; porous and non-porous organic macromolecular components, including synthetic components such as styrenedivinyl benzene beads, various methacrylate beads, PVA beads, and the like, commonly used for protein purification, water softening; and a variety of other applications, natural components such as native and functionalized celluloses, such as, for example, agarose and chitin, sheet and hollow fiber membranes made from nylon, polyether sulfone or any of the materials mentioned above. The molecular weight of these macromolecules may range up to about 2000 Daltons.

Suitable chemical modifications also include chemical bonds to a suitable organic moiety, a radioactive moiety, a hydrogen atom, an organic moiety which contains a suitable electrophilic group, such as an aldehyde, ester, alkyl halide, ketone, nitrile, epoxide or the like; a suitable nucleophilic group, such as a hydroxyl, amino, carboxylate, amide, carbanion, urea or the like; or one of the other structural diversity elements defined below. In addition, the chemical modifications can be in the form of a ring, bi-cyclic or tri-cyclic ring system; or structure which connects to the ends of the repeating unit of the compound defined by the preceding formula; or may be separately connected to other moieties.

The modifications can be the same or different and each may be one or more atoms of carbon, nitrogen, sulfur, oxygen, any other inorganic elements or combinations thereof. For example, the core structure can be modified with cyano, nitro, halogen, oxygen, hydroxy, alkoxy, thio, straight or branched chain alkyl, carbocyclic aryl and substituted or heterocyclic derivatives thereof. The modifications can be in different in adjacent molecular cores and have a selected stereochemical arrangement about the carbon atom to which they are attached.

The compounds can be laid out in a logical fashion in multi-tube arrays or multi-well plates, in the form of arrays of chemical compounds. Preferably, the compounds all have a central core structure, and have various modifications which permit the identification of structure-activity relationships with which to determine optimum compounds for a particular use.

The array can be ordered in such a fashion as to expedite synthesis, purification, and evaluation, to maximize the informational content obtained from the testing and to facilitate the rapid evaluation of that data.

The arrays can be constructed from logically ordered and arranged sub-arrays of compounds. Sub-arrays can be prepared which include spatially addressable sets of structurally related individual chemical compounds, with a common structure and a variable modification of the structure. Sub-arrays are particular useful when multiple positions on the structure are modified, and the variation between any two compounds within a given sub-array can include, for example, zero (0) or one (1) change in a structure.

These sub-arrays and arrays can be organized to form higher order arrays that include sets of arrays, and can be evaluated as a higher order array to provide information regarding the optimum structural features for the common core structure of interest.

The sub-arrays can be arranged in such a manner that the direct comparisons of compounds automatically yields information regarding the effect known fragments have on a desired application, as well as on the effect on changes in physical and reactive properties. As provided by simple set theory for any number of independently variable structural diversity elements n, there exists n logical higher order array arrangements, such that relational information on the effect of variation of each of the n structural diversity elements can be obtained in a similar manner by comparison of testing data from the relative addresses in appropriately arranged sub-arrays.

By screening all possible synthetic variations of a core molecule, the selection of the optimal candidate is more a function of the data collection method than the "rational" basis for selecting the compound. The desired physical and chemical properties, i.e., binding affinity and bioactivity, can be rapidly optimized, and directly correlated with the structural changes within a particular array or sub-array.

Because the spatial address of each compound within a multi-tube rack is known, the arrays can be tested to generate complete relational structural information such that a positive result provides: (1) information on a compound within any given spatial address; (2) simultaneous juxtaposition of this information upon a set of systematically structural congeners; (3) the ability to extract relational structural information from negative results in the presence of positive results.

Preferably, the purification is carried out via computer control, where the location of each tube in a multi-tube array or each well in a multi-well plate is stored in a computer, and the identity of the compound to be synthesized is stored in the computer in a "memory map" or other means for correlating the data for the compound to the position of the tube or well. Alternatively, the purification can be performed manually, preferably in multi-tube racks or multi-well plates, and the information stored on a computer. The compounds in the tubes can be purified and/or characterized.

The present invention will be further understood with reference to the following non-limiting examples:

EXAMPLE 1

Analytical Methods

Solutions of 16 compounds with polarities ranging from high to low polarity, with known Log P values ranging from −1.05 to 5.77, were evaluated using the conditions described below in Table 1.

The instrument used was a Gilson HPLC system with two Gilson model 306 pumps with 10 SC pump heads, Gilson 170 diode array UV detectors (254 nm), and a Gilson 215 liquid handler as the injector. An evaporated light scattering detector (Richard Scientific) and a platform LC mass spectrometer (Micromass) were used as detectors.

The mobile phase was a binary gradient of methanol/water. The stationary phase was a 4.6×50 mm column packed with 5 micron ODS-AQ. The injection size was 5 µL. The mobile phase gradient was adjusted to obtain a Log P nearly equal to the retention time on the HPLC column. The solvents and flow rates are summarized below in Table 1.

TABLE 1

| Time | Flow rate (mL/min) | Solvent A* | Solvent B** |
|---|---|---|---|
| 0 | 1.5 | 72 | 28 |
| 1 | 1.5 | 42 | 28 |
| 2 | 1.5 | 10 | 90 |
| 4 | 1.5 | 2 | 98 |
| 6 | 1.5 | 0 | 100 |
| 6.1 | 2.1 | 0 | 100 |
| 8.0 | 2.1 | 72 | 28 |
| 8.1 | 1.5 | 72 | 28 |

\* Solvent A is 98.5%/1.5% (v/v) H$_2$O/acetonitrile)
\*\* Solvent B is 100% MeOH After 6.1 minutes, the column was set to re-equilibrate.

The HPLC runs were performed in triplicate to demonstrate the reproducibility of the method. The retention time, average retention time, standard deviation (STD) and comparison with shake flask Log P values (lit. Log P) are tabulated below in Table 2.

TABLE 2

| Compound (standard #) | RT (run 1) | RT (run 2) | RT (run 3) | Avg. | Std. Dev. | Lit. Log P |
|---|---|---|---|---|---|---|
| uracil (1) | 0.29 | 0.32 | 0.29 | 0.29 | 0.015 | −1.07 |
| benzamide (2) | 0.54 | 0.51 | 0.53 | 0.53 | 0.013 | 0.64 |
| N-methyl benzamide (3) | 0.63 | 0.63 | 0.64 | 0.64 | 0.006 | 0.86 |
| benzyl alcohol (4) | 0.93 | 0.95 | 0.94 | 0.94 | 0.008 | 1.1 |
| benzene (5) | 1.87 | 1.85 | 1.85 | 1.85 | 0.010 | 1.58 |
| acetophenone (6) | 1.9 | 1.88 | 1.89 | 1.89 | 0.008 | 2.13 |

TABLE 2-continued

| Compound (standard #) | RT (run 1) | RT (run 2) | RT (run 3) | Avg. | Std. Dev. | Lit. Log P |
|---|---|---|---|---|---|---|
| bromobenzene (7) | 3.36 | 3.36 | 3.38 | 3.38 | 0.012 | 2.99 |
| p-chloro toluene (8) | 3.68 | 3.68 | 3.68 | 3.68 | 0.000 | 3.33 |
| diethyl parathion (9) | 3.77 | 3.78 | 3.79 | 3.79 | 0.010 | 3.81 |
| biphenyl (10) | 3.98 | 3.99 | 4. | 4.0 | 0.010 | 4.09 |
| 2,6-dimethyl napthalene (11) | 4.5 | 4.49 | 4.49 | 4.49 | 0.005 | 4.31 |
| anthracene (12) | 4.39 | 4.41 | 4.4 | 4.40 | 0.008 | 4.45 |
| phenyl sulfide (13) | 4.2 | 4.28 | 4.26 | 4.26 | 0.035 | 4.45 |
| trifluralin (14) | 4.8 | 4.81 | 4.81 | 4.81 | 0.005 | 5.34 |
| methoxychlor (15) | 4.48 | 4.55 | 4.54 | 4.54 | 0.032 | 4.68 |
| DDE (16) | 5.5 | 5.51 | 5.5 | 5.50 | 0.005 | 5.77 |

As shown in Table 2, the method is reproducible. When the retention times are plotted against the known Log P values, there is a linear correlation, as shown in FIG. 1. The slope of the line is 1.0088, and the y intercept is 0.0268.

Retention times (X), shake flask log P (Y), slope and intercept from the above plot were used to calculate log P for these standards. The results, shown below in Table 3, show that the retention time, multiplied by the slope and added to the y intercept, provide a Log P value extremely close to the literature value, except for uracil, which is a highly polar compound. Such compounds are known to be highly polar.

TABLE 3

| New Method RT (min) (standard #) | Calc. Log P Y = 1.009X + 0.029 | Lit. Log P | Isocratic Log P | Predicted Log P |
|---|---|---|---|---|
| 0.29 (1) | 0.32 | −1.07 | −1.05 | |
| 0.53 (2) | 0.56 | 0.64 | 0.41 | 0.66 |
| 0.64 (3) | 0.68 | 0.86 | 0.96 | 0.86 |
| 0.94 (4) | 0.98 | 1.1 | 0.96 | 1.1 |
| 1.85 (5) | 1.90 | 1.58 | 1.99 | 1.58 |
| 1.89 (6) | 1.94 | 2.13 | 2.54 | 2.64 |
| 3.38 (7) | 3.44 | 2.99 | 3.23 | 3 |
| 3.68 (8) | 3.74 | 3.33 | 3.57 | 3.35 |
| 3.79 (9) | 3.85 | 3.81 | 3.39 | 3.2 |
| 4.00 (10) | 4.07 | 4.09 | 3.8 | 4.03 |
| 4.49 (11) | 4.56 | 4.31 | 4.49 | 4.31 |
| 4.40 (12) | 4.47 | 4.45 | 4.46 | 4.49 |
| 4.26 (13) | 4.33 | 4.45 | 4.31 | 4.48 |
| 4.81 (14) | 4.88 | 5.34 | 5 | 5.02 |
| 4.54 (15) | 4.61 | 4.68 | 4.26 | 4.45 |
| 5.50 (16) | 5.58 | 5.77 | 6.28 | 5.73 |

Figure 2:
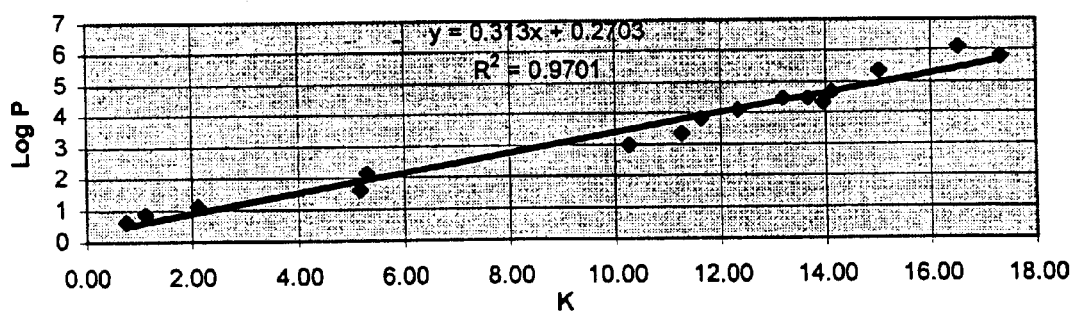
FIG. 2 is a plot of log P versus capacity factor for a series of standards.
Figure 3:
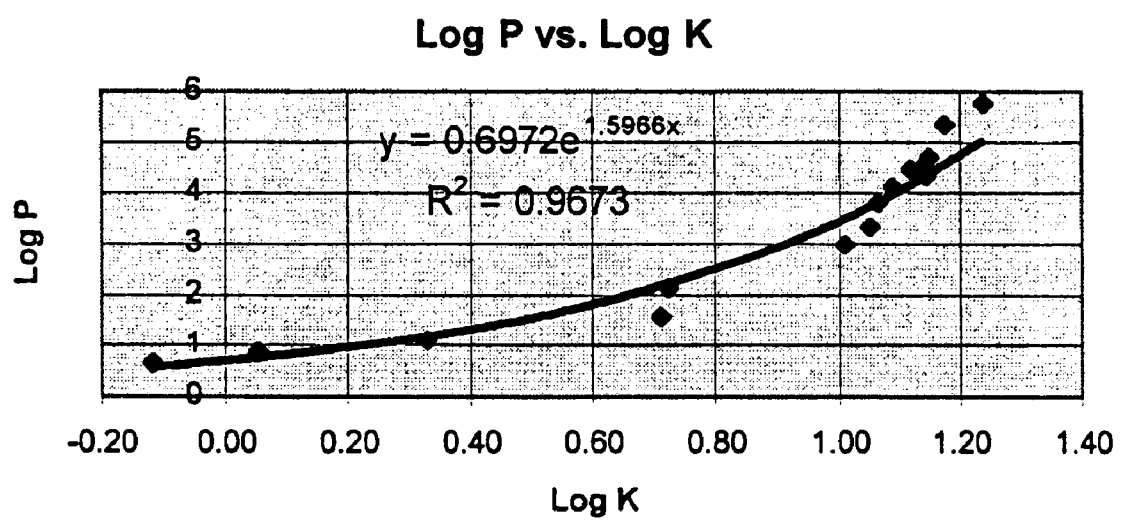
FIG. 3 is a plot of Log P versus Log K for a series of standards.

A plot of log P versus the capacity factor K (K=t−t0/t0) for these compound produced a linear plot, as shown in FIG. 2. When log P was plotted versus the log of the capacity factor K for these standards, an following exponential curve was obtained, as shown in FIG. 3.

Using this exponential equation and HPLC retention times of these standards, Log P and Log K were calculated and compared with the retention times and literature Log P values. The results are summarized below in Table 4.

TABLE 4

| Log K (standard #) | Log P calc. by slope | RT | Lit. Log P |
|---|---|---|---|
| −0.12 (2) | 0.58 | 0.53 | 0.64 |
| 0.05 (3) | 0.75 | 0.64 | 0.86 |
| 0.33 (4) | 1.18 | 0.94 | 1.1 |
| 0.71 (5) | 2.18 | 1.85 | 1.58 |
| 0.72 (6) | 2.22 | 1.89 | 2.13 |
| 1.01 (7) | 3.50 | 3.38 | 2.99 |
| 1.05 (8) | 3.74 | 3.68 | 3.33 |
| 1.07 (9) | 3.82 | 3.79 | 3.81 |
| 1.09 (10) | 3.98 | 4.00 | 4.09 |
| 1.15 (11) | 4.34 | 4.49 | 4.31 |
| 1.14 (12) | 4.27 | 4.40 | 4.45 |
| 1.12 (13) | 4.17 | 4.26 | 4.45 |
| 1.18 (14) | 4.57 | 4.81 | 5.34 |
| 1.15 (15) | 4.37 | 4.54 | 4.68 |
| 1.24 (16) | 5.04 | 5.50 | 5.77 |

The calculation is as follows:

$$Y = 0.6972 e^{1.5966 X}$$

$$R^2 = 0.9673$$

As shown in the Table 4, there is a reasonable correlation between the Log P values calculated using the exponential equation, by retention time and the literature Log P values from the shake flask method.

The void volume (Vo) and void time (t0) for ODS-AQ, 4.6×50 mm (a C18 reverse phase column manufactured by YMC) are reasonably small.

The following equations can be used to calculate Vo and t0.

$$V0 = 0.65 \times 3.14 (d/2)^2 L,$$

where d is column internal diameter (ID) in cm, and L is column length (mm)

$$\text{void time } (t0) = V0/F,$$

where F is the flow rate (mL/min)

According to the above V0 and t0 equations, void volume and void time for the column is about 0.5 mL and 0.35 minutes, respectively. In practice, these numbers were typically about 0.38 mL and 0.25 minutes.

Those skilled in the art will recognize, or be able to ascertain using no more than routine experimentation, many equivalents to the specific embodiments of the invention described herein. Such equivalents are intended to be encompassed by the following claims.

What is claimed is:

1. A method for calculating log P values for one or more compounds, comprising:
   a) determining an appropriate set of HPLC conditions such that the log P value is substantially equal to the retention time on an HPLC column, and
   b) determining the log P values of one or more compounds by eluting them off of the HPLC column under the set of HPLC conditions determined in step (a).

2. The method of claim 1 wherein the purity of the compound or compounds and the Log P value(s) are determined simultaneously.

3. The method of claim 1 wherein the compounds to be analyzed are present in a combinatorial or lead generation library.

4. The method of claim 1 wherein the compounds are detected and/or characterized by one or more methods selected from the group consisting of UV, MS and ELSD.

5. The method of claim 1, wherein the one or more compounds are eluted off of the HPLC column using gradient elution.

6. A method for calculating log P values for one or more compounds, comprising:
   a) determining an appropriate set of HPLC conditions such that the log P value is substantially equal to the retention time on an HPLC column;
   b) determining the log P values of one or more compounds by eluting them off of the HPLC column under the set of HPLC conditions determined in step (a); and
   c) characterizing the one or more compounds, wherein only the one or more compounds with a desired log P value are characterized.

7. The method of claim 6, wherein characterizing the one or more compounds comprises performing a bioassay on the one or more compounds to determine their bioactivity and wherein only the one or more compounds with a desired Log P value are bioassayed.

8. The method of claim 6, wherein information regarding the Log P values and the characterization of the one or more compounds is stored in a database.

9. The method of claim 6, wherein the one or more compounds are eluted off of the HPLC column using gradient elution.

10. The method of claim 6, wherein purity of the one or more compounds is determined simultaneously with the log P values of the one or more compounds.

11. The method of claim 7, wherein the one or more compounds are eluted off of the HPLC column using gradient elution and wherein information regarding the Log P values and the bioactivity of the one or more compounds is stored in a database.

12. The method of claim 11, wherein purity of the one or more compounds is determined simultaneously with the log P values of the one or more compounds.

* * * * *